United States Patent [19]

Rosen

[11] 4,066,666
[45] Jan. 3, 1978

[54] 15-OXASTEROIDS
[75] Inventor: Perry Rosen, North Caldwell, N.J.
[73] Assignee: Hoffmann-La Roche Inc., Nutley, N.J.
[21] Appl. No.: 702,243
[22] Filed: July 2, 1976

Related U.S. Application Data

[62] Division of Ser. No. 528,115, Nov. 29, 1974, Pat. No. 3,987,066, which is a division of Ser. No. 217,956, Jan. 14, 1972, Pat. No. 3,872,076.
[51] Int. Cl.$^2$ .................. C07D 317/72; C07D 319/04
[52] U.S. Cl. .......................... 260/340.9 AS; 260/141; 260/326.13 R; 260/514.5; 424/285
[58] Field of Search ................... 260/340.9 AS, 340.7

[56] References Cited
PUBLICATIONS

Chem. Abstracts, 79:92459p.
Chem. Abstracts, 79:P92482r.

*Primary Examiner*—Ethel G. Love
*Attorney, Agent, or Firm*—Samuel L. Welt; George M. Gould; Raymond R. Wittekind

[57] ABSTRACT

15-Oxasteroids of the androstane, pregnane, estrane, and 19-norpregnane series are useful as hormonal agents.

3 Claims, No Drawings

15-OXASTEROIDS

This is a division of application Ser. No. 528,115 filed Nov. 29, 1974, now U.S. Pat. No. 3,987,066, which is a division of application Ser. No. 217,956, filed Jan. 14, 1972, now U.S. Pat. No. 3,872,076.

BRIEF DESCRIPTION OF THE INVENTION

The present invention relates to novel compounds represented by the formula

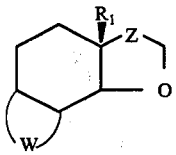

I wherein $R_1$ is lower alkyl of from 1 to 5 carbon atoms; W is one of the partial formulas

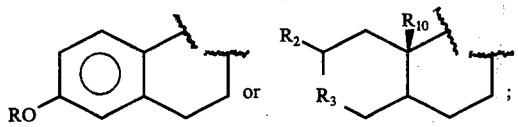

where R is hydrogen, lower alkyl, cycloalkyl, lower alkanoyl or aroyl; $R_2$ taken independently is hydrogen; $R_3$ taken independently is a 3-hydroxy, 3-lower alkanoyloxy, 3-keto or 3-keto-$\Delta^4$ group; and $R_2$ and $R_3$ taken together with carbon atoms 2 and 3 of the steroid nucleus represent a 5-membered heteroaromatic ring wherein one heteroatom is attached to carbon atom 3; $R_{10}$ is hydrogen or methyl; and Z is one of the groups carbonyl, ketal protected carbonyl,

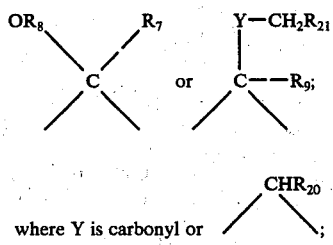

$R_7$ is hydrogen, lower alkyl, lower alkenyl or lower alkynyl; $R_8$ is hydrogen, lower alkyl, cycloalkyl, lower alkanoyl or aroyl; $R_9$ is hydrogen, hydroxy, or lower alkanoyloxy; $R_{20}$ is hydroxy or lower alkanoyloxy; and $R_{21}$ is hydrogen, hydroxy, lower alkanoyloxy or halogen.

More specifically, the present invention is concerned with the two classes of subgeneric steroids represented by the formulas Ia and Ib

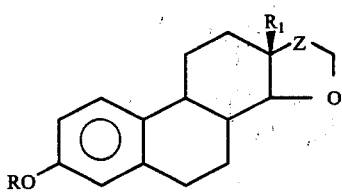

Ia

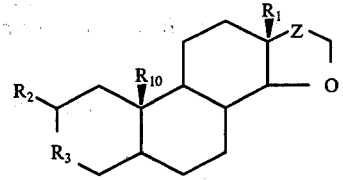

Ib wherein R, $R_1$, $R_2$, $R_3$, $R_{10}$ and Z are as above.

As used throughout the specification and the appended claims, the term "alkyl group" refers to a monovalent radical of up to 20 carbon atoms consisting solely of carbon and hydrogen and containing no unsaturation; the term "alkenyl group" refers to a monovalent radical consisting solely of carbon and hydrogen of up to 20 carbon atoms containing olefinic unsaturation; the term "alkynyl group" refers to a monovalent radical consisting solely of carbon and hydrogen of up to 20 carbon atoms containing acetylenic unsaturation. The term "cycloalkyl group" denotes a monovalent radical consisting solely of carbon and hydrogen possessing at least one carbocyclic ring, said ring containing from 3 to 8 carbon atoms. The term "alkanoyl" refers to the residue of a saturated aliphatic carboxylic acid containing up to 20 carbon atoms obtained by removing the hydroxyl from the carboxyl moiety. The term "alkanoyloxy group" refers to the residue of a saturated aliphatic carboxylic acid containing up to 20 carbon atoms obtained by removal of the hydrogen from the carboxyl moiety. The term "aroyl" refers to the residue of a monocyclic aromatic carboxylic acid obtained by removing the hydroxyl from the carboxyl moiety. The term "halogen" refers to fluorine, chlorine, bromine and iodine. The term "ketal protected carbonyl" refers to a group which may be hydrolyzed to regenerate a carbonyl group under conventional hydrolysis conditions, such as a carbonyl protected as a di(lower alkyl)ketal, an alkylene ketal or an arylene ketal. Examples of di(-lower alkyl)ketals are dimethyl ketals, diethyl ketals and so forth. Alkylene ketals are derived from 1,2 or 1,3 glycols, e.g. ethylene glycol, 1,3-propyleneglycol, 2,3-butyleneglycol and so forth. Arylene ketals are derived from catechols, e.g. phenylene-1,2-diol, alkyl-substituted-phenylene-1,2-diols, naphthalene-1,2- or 2,3-diols, and so forth. The term "heteroaromatic ring" comprehends a monocyclic ring system having aromatic unsaturation and which has at least one ring member which is not a carbon atom. The term "lower", as applied to any of the foregoing groups, denotes a group having a carbon skeleton containing up to and including 8 carbon atoms.

In the formulas presented herein, the various substituents on cyclic compounds are joined to the cyclic nucleus by one of three notations: a solid line (—) indicating a substituent which is in the $\beta$-orientation (i.e., above the plane of the paper), a dotted line (- - - -) indicating a substituent which is in the $\alpha$-orientation (i.e., below the plane of the paper), a wavy line (〜) indicating a substituent which is in either the $\alpha$- or the $\beta$-orientation. Although the position of the angular methyl group at carbon atom 13 of the steroid nucleus has been arbitrarily indicated as the $\beta$-orientation, i.e., the "natural" steroid series, the invention is not to be construed as limited to the "natural" steroid series and is meant to include the corresponding "unnatural" and racemic series of steroids.

The 15-oxasteroids represented by formulas Ia and Ib can be prepared from the corresponding carboxylic 17-oxosteroids, as depicted in Reaction Scheme A below.

REACTION SCHEME A

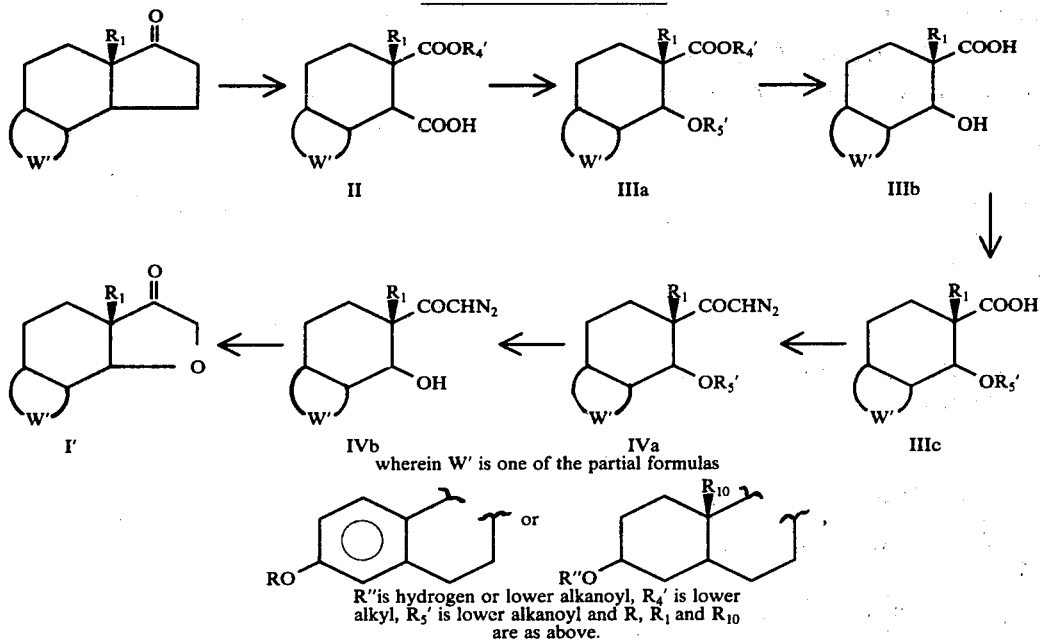

wherein W' is one of the partial formulas

R" is hydrogen or lower alkanoyl, R$_4$' is lower alkyl, R$_5$' is lower alkanoyl and R, R$_1$ and R$_{10}$ are as above.

Compounds of formula II are known and are prepared from 17-keto-steroids by oxidative cleavage of the D-ring by methods known per se. Compounds of formula III

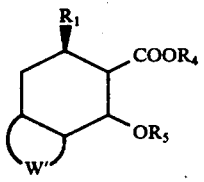

III wherein
R$_4$ is hydrogen or lower alkyl,
R$_5$ is hydrogen or lower alkanoyl and
R$_1$ and W' are as above,
are novel and constitute part of the present invention.

The preparation of a compound falling within the genus of formula IIIa purported to be 3β,14-diacetoxy-14,17-seco-D-bis-norandrostan-17-oic acid 17-methyl ester has been described by Banerjee and Gut, *J. Org. Chem.*, 34, 1614 (1969). The material was prepared via a series of reactions from a compound purported to be 3β-acetoxy-15,17-seco-D-norandrostan-15,17-dioic acid 17-methyl ester, a compound falling within the genus of formula II.

During the course of the present invention it has been discovered that both above compounds are erroneously described. It has been shown that the starting diacid monomethyl ester was in reality 3β-acetoxy-15,17-seco-D-norandrostan-15,17-dioic acid 15-methyl ester and the degradation product prepared therefrom 3β,13-diacetoxy-13,15-seco-D-bisnorandrostan-15-oic acid 15-methyl ester. The preparation of 3β-acetoxy-15,17-seco-D-norandrostan-15,17-dioic acid 17-methyl ester, agreeing in physical properties with that prepared herein, was described by Fetizon and Moreau, *Bull. Soc. Chim. France*, 4385 (1969). Furthermore, it has been demonstrated that the series of reactions described by Banerjee and Gut as leading from their dioic acid dimethyl ester to their monomethyl ester acetate is not operative for the analogous conversion of compound II to compound IIIa.

According to the present invention, the degradation of a compound of formula II to one of formula IIIa is suitably effected by contacting the former with a tetra(alkanoyloxy)lead, most preferably lead tetraacetate. This reaction is generally carried out in the presence of a weak base, for example, an organic amine, preferably pyridine. An inert organic solvent is suitably employed as a diluent, preferably a hydrocarbon such as benzene or toluene. A temperature of from about 40° to about 150° C. may be employed although it is generally preferred to carried out the reaction at the reflux temperature of the reaction medium.

In the next step, compound IIIa is hydrolyzed to the hydroxy acid of formula IIIb. Where R or R" in partial formula W' is lower alkanoyl or aroyl, these groups are also hydrolyzed to a hydroxy group under the reaction conditions. Suitable reaction conditions are readily suggested to one skilled in the art, and include heating a compound of formula IIIa with a dilute alcoholic solution of an alkali metal hydroxide, e.g. refluxing with a 3% methanolic potassium hydroxide solution.

The hydroxy group at carbon atom 14 (and, if present, one at carbon atom 3) may then be reacylated by treatment with the desired acid chloride or anhydride to afford a compound of formula IIIc. The next step is the preparation of a diazo ketone of formula IV

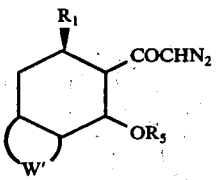

IV wherein $R_1$, $R_5$ and W' are as above.

Accordingly, the carboxyl group of the alkanoyloxy acid of formula IIIc is converted to a diazo ketone moiety by treatment of an activated derivative of the acid with diazomethane. Suitable activated acid derivatives include acid halides, most preferably the acid chloride. The conversion to the diazoketone is suitably effected by contacting a solution of the acid halide in an inert organic solvent, e.g. an ether, with an excess of diazomethane, in the cold. Suitably, the reaction is carried out at about 0° to prevent evaporation of the low boiling diazomethane.

The 14-acyloxy group of the diazo ketone of formula IVa, as well as any acylated hydroxyl groups present at carbon atom 3, are next hydrolyzed to the free hydroxy groups by alkaline saponification. Suitable saponification agents include alkali metal hydroxides, e.g. sodium hydroxide and potassium hydroxide. Saponification is suitably carried out in an inert organic solvent preferably an alcohol, e.g. methanol or ethanol. A suitable reaction temperature is about room temperature.

The diazo ketone alcohol of formula IVb is next cyclized to afford the 15-oxasteroid of formula I. This cyclization reaction is carried out in the presence of an acidic cyclization catalyst. Suitable acidic cyclization catalysts include Lewis acids, most preferably boron trifluoride and its ether complexes. The cyclization reaction is suitably performed in any anhydrous inert organic solvent; preferred organic solvents include hydrocarbons, e.g. benzene and toluene. The cyclization is preferably effected at a temperature between about 0° and about 40° C., most preferably about room temperature. The reaction may be monitored by following the evolution of nitrogen, and is continued until this evolution is substantially complete.

The compounds of formula I', thus formed, may be further converted to the remaining members of the genus represented by formula I by standard transformations at the 3- and 17-positions.

Members of the subgenuses Ia and Ib may be interconverted by a number of procedures well known in the art. For example, the A-ring aromatic 15-oxasteroids represented by formula Ia, may be converted to 19-nor-15-oxasteroids, represented by formula Ib where $R_{10}$ is hydrogen by, for example, Birch reduction of the aromatic ring and subsequent hydrolysis of the resulting enol ether. In another procedure, 15-oxa-androstanes of formula Ib where $R_{10}$ is methyl may be converted to 15-oxaestrone derivatives of formula Ia by aromatization of the A-ring according to well known procedures.

Compounds of formula I' having a 17-keto group may be converted to the corresponding pregnanes by addition of the requisite 2-carbon side chain at the 17-position by methods known per se for 17-keto steroids.

The conversion of the 17-keto group to other moieties represented by the substituent Z may be accomplished in the normal manner utilized for carbocyclic 17-keto steroids, for example, by reduction of the carbonyl group to a 17β-hydroxyl function and optional acylation; or by addition of an organometallic reagent to introduce a 17α-alkyl, alkenyl or alkynyl group; and so forth. The $R_3$ function in compounds of formula Ib may be modified according to standard procedures known in the art involving, for example, oxidation of the 3-hydroxy to a 3-ketone; introduction of a Δ⁴-double bond; and so forth.

Compounds of formula Ib wherein $R_3$ is a 3-keto or 3-keto-Δ⁴ function, may be converted, according to well known procedures, to steroids having a heterocyclic ring fused to the 2- and 3-positions of the A-ring. For example, 3-keto-15-oxasteroids of formula Ib may be converted, via the 2-hydroxymethylene derivatives, to the corresponding [2,3-d] or [3,2-c]-isoxazoles or [3,2-c]pyrazoles.

Preferred compounds of the present invention are those of subgenus Ia. Particularly preferred are those wherein $R_1$ is methyl, Z is carbonyl or β-hydroxymethylene and R is hydrogen or a cycloalkyl group.

The compounds of formula I exhibit hormonal activity. In particular, compounds of formula Ia are potent estrogens when tested in the standard estrogenic (uterotrophic) assay. In this test, the test compound is administered once daily for 3 consecutive days to a group of 10 immature female rats. Uteri are removed by autopsy on the fourth day and weighed on a torsion balance and the organ ratio (mg. organ/100 g. body weight) is calculated for each rat and the mean determined for each group. The percent difference from the value for the control group is computed. By way of example, 15-oxaestrone, when tested in the above assay exhibits an oral estrogenic activity approximately 12 times that of estrone, and approximately twice that of Mestranol. These compounds are thus useful in the treatment of various conditions in which estrogenic agents are indicated such as estrogen deficiencies, menopause, and the like. The compounds of formula Ia may also be utilized in conjunction with a progestational agent for the control of fertility.

Compounds of formula Ib wherein Z is carbonyl or the group

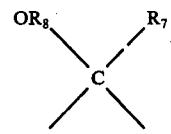

exhibit androgenic/anabolic activity in the standard levator ani and ventral prostrate assays. Compounds of formula Ib wherein Z is

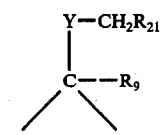

exhibit progestational activity in the standard Clauberg assay.

Compounds of formula I can be administered internally, for example, orally or parenterally, with dosages adjusted to individual requirements. Compounds of formula I may be administered in unit or divided dosages to make up the daily dosage regimens. The selection of the specific dosages and dosage regimens should be left to the discretion of the trained medical practitioner. By way of example, an approximate daily dosage for 15-oxaestrone in an adult human would be from about 0.01 to about 1.0 mg. per day.

The above compounds of formula I can be administered in the form of conventional pharmaceutical preparations; for example, they can be administered in conventional pharmaceutical solid or liquid forms, such as tablets, pills, capsules, solutions, suspensions, emulsions or the like. These pharmaceutical preparations can contain conventional pharmaceutical carriers and excipients such as water, talc, corn starch, polyalkylene glycol, emulsifying agents, buffering agents, agents for the adjustment of osmotic pressure, vaseline and the like. The pharmaceutical compositions described above can additionally contain other active ingredients.

The following examples serve to further illustrate the practice of the present invention and are not to be construed in any sense as limitative thereof.

EXAMPLE 1

3β-Hydroxy16,17-seco-16-norandrostan-15-(2'-indoxyliden)-17-oic acid

To a solution of 400 g. (1.38 mole) of isoandrosterone in 6 l. of 3% methanolic potassium hydroxide was added 275 g. (1.82 mole) of o-nitrobenzaldehyde. The mixture was stirred at room temperature under nitrogen for 18 hours, then concentrated under vacuum to a volume of approximately 2 l. The solution was then cooled and with stirring acidified with 1.2 l. of 3N hydrochloric acid. The resulting yellow precipitate was collected by filtration, washed thoroughly with water and dried. The product was then stirred in 2 l. of cold acetone, filtered and dried to give 356 g. of 3β-hydroxy-16,17-seco-16-norandrostan15(2'-indoxyliden)-17-oic acid, mp 272°–274°.

EXAMPLE 2

3β-Hydroxy-16,17-seco-16-norandrostan-15-(2'-indoxyliden)-17-oic acid 17-methyl ester To a mixture of 356 g. of 3β-hydroxy-16,17-seco-16-norandrostan-15-(2'-indoxyliden)-17-oic acid in 3 l. of methanol was added dropwise 40 ml. of acetyl chloride. After refluxing for 4 hours, the methanol was removed under reduced pressure and 2 l. of water was added to the residue. The resulting precipitate was filtered, washed with water and dried. The product was then dissolved in a minimum of methylene chloride and treated with Norit and dried (MgSO$_4$). The mixture was filtered and the methylene chloride removed under reduced pressure. Trituration of the residue with ether afforded 325 g. of 3β-hydroxy-16,17-seco-16-norandrostan-15-(2'-indoxyliden)-17-oic acid 17-methyl ester, mp 258°–261°.

EXAMPLE 3

3β-Acetoxy-16,17-seco-16-norandrostan-15-(2'-indoxyliden)-17-oic acid 17-methyl ester A solution of 325 g. of 3β-hydroxy-16,17-seco-16-norandrostan-15-(2'-indoxyliden)-17-oic acid 17-methyl ester, 325 ml. of acetic anhydride and 1300 ml. of pyridine was stirred overnight. The mixture was divided into three portions and each then added to 3 l. of cold (0°) 3N hydrochloric acid. The resulting precipitates were filtered and the combined product washed with water and dried to give 350 g. of 3β-acetoxy-16,17-seco-16-norandrostan-15-(2'-indoxyliden)-17-oic acid 17-methyl ester, mp 260°–262°.

EXAMPLE 4

3β-Acetoxy-15,17-seco-D-norandrostane-15,17-dioic acid 17-methyl ester

To a suspension of 350 g. of 3β-acetoxy-16,17-norandrostan-15-(2'-indoxyliden)-17-oic acid 17-methyl ester in 5 l. of glacial acetic acid was added dropwise 290 ml. of a 90% aqueous chromium trioxide solution prepared by dissolving 90G chromium trioxide in 100 ml. water. Solution soon occurred with the evolution of heat (the temperature was kept below 70° with external cooling). After stirring overnight the acetic acid was removed under high vacuum and the residue treated with 4 l. of water. The precipitate was filtered, washed thoroughly with water and dried. The product was then dissolved in benzene and the solution treated with Norit and anhydrous magnesium sulfate. The mixture was filtered and the benzene removed under reduced pressure. Trituration of the residue with hexane afforded 255 g. of 3β-acetoxy-15,17-seco-D-norandrostane-15,17-dioic acid 17-methyl ester, mp 152°–158°.

EXAMPLE 5

A mixture of 255 g. of 3β-acetoxy-15,17-seco-D-norandrostane-15,17-dioic acid 17-methyl ester, 745 g. of lead tetra-acetate (dried in vacuo over P$_2$O$_5$), 108 ml. of pyridine and 3.8 l. of dry benzene was stirred and refluxed for 7 hours. The mixture was cooled and the lead salts filtered and thoroughly washed with ether. The filtrate was washed with a 10% solution of sodium thiosulfate, 1N hydrochloric acid and then a saturated sodium chloride solution. The solution was dried (MgSO$_4$) and the solvent removed under reduced pressure to give 270 g. of crude product. This material was dissolved in a minimum of benzene and washed through 1300 g. of neutral Alumina (grade 1). Elution with 3 l. of benzene followed by 1 l. of a 1% ethyl acetate benzene solution afforded 215 g. of crude material. This product was then dissolved in 1230 ml. of 3% methanolic potassium hydroxide and stirred at 0° for 1 hour. The mixture was acidified with 700 ml. of 1N hydrochloric acid at 0° and the precipitate filtered and dried to give 108 g. of 3β-hydroxy-14β-acetoxy-14,17-seco-D-bisnorandrostan-17-oic acid 17-methyl ester, mp 127°–130°. The methanol was removed from the filtrate under reduced pressure and the mixture extracted with methylene chloride and the resulting solution dried (MgSO$_4$). The solvent was removed under reduced pressure and the residue triturated with methanol to give 2 g. of 3β-hydroxy-14β-acetoxy-14,17-seco-D-norandrostan-17-oic acid 17-methyl ester, mp 126°–130°. A third crop of 3 g., mp 124°–128°, was obtained by removing a portion of the methanol under reduced pressure. Crystallization from methanol afforded an analytical sample containing one mole of methanol, mp 134°–136° $[\alpha]_D^{25}$ −164.76° (c, 1.11%, CHCl$_3$).

Anal. Calcd. for C$_{21}$H$_{36}$O$_6$: C, 65.59; H, 9.44. Found: C, 65.85; H, 10.09.

Acetylation with pyridine-acetic anhydride afforded 3β,14β-diacetoxy-14,17-seco-D-bisnorandrostan-17-oic acid 17-methyl ester, mp 105°–106°, $[\alpha]_D^{25}$ −16.23° (c, 0.758%, CHCl$_3$).

Anal. Calcd. for C$_{22}$H$_{34}$O$_6$: C, 66.98; H, 8.69. Found: C, 67.11; H, 8.93.

EXAMPLE 6

3β,14β-Dihydroxy-14,17-seco-D-bisnorandrostan-17-oic acid

A solution of 86 g. of 3β-hydroxy-14β-acetoxy-14,17-seco-D-bisnorandrostan-17-oic acid 17-methyl ester in 2.74 l. of 3% methanolic potassium hydroxide was refluxed for 6 hours. The methanol was removed under reduced pressure and 200 ml. of water added to the residue. The solution was cooled to 0° and acidified with concentrated hydrochloric acid. The precipitate was filtered and dried to give 72.2 g. of 3β,14β-dihydroxy-14,17-seco-P-bis norandrostan-17-oic acid, mp 285°-287°. Crystallization from methanol afforded an analytical sample, mp 285°-287°, $[\beta]_D^{25}$ +11.94° (c, 0.9047%, CH$_3$OH).

Anal. Calcd. for C$_{17}$H$_{28}$O$_4$: C, 68.88; H, 9.52. Found: C, 69.16; H, 9.71.

EXAMPLE 7

3β,14β-Dihydroxy-16-diazo-17-oxo-14,16-seco-D-norandrostane

To a solution of 350 ml. of acetic anhydride in 350 ml. of pyridine was added 70 g. of 3β,14β-dihydroxy-14,17-seco-D-norandrostan-17-oic acid. The solution was stirred at room temperature overnight and then poured into 6 l. of ice water. The mixture was stirred for 2 hours and then extracted with ether. The ether solution was washed with 1N hydrochloric acid and then water until neutrality. The solution was dried (MgSO$_4$) and the solvent removed under reduced pressure to give 83 g. of crude 3β,14β-diacetoxy-14,17-seco-D-bisnorandrostan-17-oic acid as an oil.

The crude diacetate (83 g.) was treated with 90 ml. of oxalyl chloride and stirred at room temperature overnight. The excess oxalyl chloride was then removed under reduced pressure and the residue diluted with hexane and the solvent again removed under reduced pressure to give 85 g. of crude acid chloride.

To an ethereal solution of diazomethane prepared from 150 g. of N-methylnitrosourea was added dropwise with stirring at 0° a solution of 85 g. of the crude acid chloride in 200 ml. of ether. The solution was stirred at 0° for 2 hours and the solvent and excess diazomethane then evaporated under a stream of nitrogen to afford 3β,14β-diacetoxy-16-diazo-17-oxo-14,16-seco-D-norandrostane. This diazoketone was then added to 790 ml. of a 6% methanolic potassium hydroxide solution and stirred at room temperature for 5 hours. The reaction mixture was then cooled to 5° and the precipitate filtered to give 63 g. of 3β,14β-dihyroxy-16-diazo-17-oxo-14,16-seco-D-norandrostane, mp 145°-150°. Crystallization from ether-methylene chloride afforded an analytical sample, mp 154°-156°, $[\alpha]_D^{25}$ −8.46° (c, 0.9697%, CHCl$_3$).

Anal. Calcd. for C$_{18}$H$_{28}$N$_2$O$_3$: C, 67.47; H, 8.81 Found: C, 67.22; H, 8.91.

EXAMPLE 8

3β-Hydroxy-15-oxa-5α-androstan-17-one

To a suspension of 63 g. of 3β,14β-dihydroxy-16-diazo-17-oxo-14,16-seco-D-norandrostane in 1.2 l. of dry benzene was added dropwise with stirring a solution of 15 ml. of boron trifluoride-etherate in 20 ml. of benzene. The evolution of nitrogen began immediately, and after the addition was completed (∼15 minutes) the reaction was stirred for an additional 10 minutes. The benzene solution was then washed with 5% sodium bicarbonate solution and the aqueous extracts backwashed with ether. The organic layers were then combined, dried (MgSO$_4$), heated with Norit and then filtered. The solvent was removed under reduced pressure and the residue triturated with hexane to give 54.5 g. of 3β-hydroxy-15-oxa-5α-androstan-17-one, mp 145°-150°. Crystallization from ether-methylene chloride afforded an analytical sample, mp 152°-154°, $[\alpha]_D^{25}$ +54,07°(c, 0.505%, CHCl$_3$).

Anal. Calcd. for C$_{18}$H$_{28}$O$_3$: C, 73.93; H, 9.65. Found: C, 73.90; H, 9.82.

Acetylation with pyridine-acetic anhydride followed by crystallization from methanol afforded the 3-acetoxy derivative, mp 164°-167°, $[\alpha]_D^{25}$ +45.19°(c, .9249%, CHCl$_3$).

Anal. Calcd. for C$_{20}$H$_{30}$O$_4$: C, 71.82; H, 9.04. Found: C, 71.56; H, 8.86.

EXAMPLE 9

15-Oxa-5α-androstan-3,17-dione

To a cooled (0°) solution of 10 g of 3β-hydroxy-15oxa-5α-androstan-17-one in 100 ml. of acetone was added dropwise with stirring 10 ml. of Jones reagent. After the addition was complete the mixture was stirred at 0° for 10 minutes. The solvent was then removed under reduced pressure and the residue treated with 300 ml. of ice water. The precipitate was filtered and washed thoroughly with water and dried. The product was then dissolved in a minimum of methylene chloride and the solution treated with Norit and filtered. The solvent was removed under reduced pressure to give 9.2 g. of 15oxa-5α-androstan-3,17-dione, mp 176°-180°. Crystallization from ether-methylene chloride afforded an analytical sample, mp 182°-185°, $[\alpha]_D^{25}$ +77.39°(c, 1.1798%, CHCl$_3$).

Anal. Calcd. for C$_{18}$H$_{26}$O$_3$: C, 74.44; H, 9.03. Found: C, 74.18; H, 9.01.

EXAMPLE 10

2α,4α-Dibromo-15oxa-5α-androstan-3,17-dione

To a solution of 16.5 g. of 15-oxa-5α-androstan-3,17-dione in 160 ml. of dry tetrahydrofuran was added 216 g. of phenyltrimethylammonium perbromide. The brominating agent quickly dissolved and after a short time phenyltrimethylammonium bromide began to precipitate. The mixture was stirred for 4.5 hours and the precipitate filtered and washed with benzene. An additional 100 ml. of benzene was added to the filtrate and the resulting solution was then washed with a 5% solution of sodium sulfite, water and then dried (MgSO$_4$). The solvent was removed under reduced pressure and the residue triturated with cold ether to give 14.2 g. of 2α,4α-dibromo-15-oxa-5α-androstan-3,17-dione, mp 212°-214°. Crystallization from methylene chloride-ether afforded an analytical sample, mp 213°-215° d, $[\alpha]_D^{25}$ +18.05° (c, 0.9861%, CHCl$_3$).

Anal. Calcd. for C$_{18}$H$_{24}$Br$_2$O$_3$: C, 48.24; H, 5.40. Found: C, 48.20; H, 5.50.

EXAMPLE 11

15-Oxa-1,4-androstadiene-3,17-dione

To a solution of 19.6 g. of lithium bromide and 19.6 g. of lithium carbonate in 200 ml. of dry dimethylformamide at 95° was added dropwise a solution of 14.7 g. of 2α,4α-dibromo-15-oxa5α-androstan-3,17-dione in 150 ml. of the same solvent. The mixture was stirred and maintained at 95° for 18 hours and most of the dimethylformamide was then removed under high vacuum. To the residue was then added 200 ml. of ice water followed by 50 ml. of 1N hydrochloric acid. The precipitated semi-solid was then extracted with methylene chloride and the organic layer washed thoroughly with water and dried (MgSO$_4$). The solvent was then removed under reduced pressure and the residue dissolved in a minimum of methylene chloride and passed through 50 g. of neutral alumina (grade 1). Elution with methylene chloride gave 9.5 g. of crude product which when triturated with ether afforded 7 g. of 15-oxa-1,4-androstadiene-3,17-dione, mp 181°–185°. Crystallization from methylene chloride-ether afforded an analytical sample, mp 185°–187°, $[\alpha]_D^{25}$ +70.50° (c, 0.9050%, $CHCl_3$).

Anal. Calcd. for $C_{18}H_{22}O_3$: C, 75.49; H, 7.74. Found: C, 75.77; H, 7.97.

EXAMPLE 12

15-Oxa-1,4-androstadiene-3,17-dione-17-ethylene ketal

A mixture of 7 g. of 15-oxa 1,4-androstadiene-3,17-dione, 14 ml. of ethylene glycol, 0.28 g. of p-toluenesulfonic acid and 350 ml. of benzene was placed in a 500 ml. flask fitted with a Soxhlet extractor which was charged with Linde 3A molecular sieves. After refluxing for 6 hours, the reaction was cooled and washed with a 5% sodium bicarbonate solution, water, and dried ($Na_2SO_4$). The solvent was removed under reduced pressure and the residue triturated with ether to give 6.5 g. of 15-oxa-1,4-androstadiene-3,17-dione-17-ethylene ketal, mp 147°–150°. Crystallization from methylene chloride-ether afforded an analytical sample, mp 147°–150°, $[\alpha]_D^{25}$ +6.50° (c, 0.9545%, $CHCl_3$).

Anal. Calcd. for $C_{20}H_{26}O_4$: C, 72.70; H, 7.93. Found: C, 72.76; H, 7.89.

EXAMPLE 13

15-Oxaestrone-17-ethylene ketal

To a solution of 86.2 g. of biphenyl in 1.5 l. of dry tetrahydrofuran was added 4.35 g. of lithium wire. The mixture was stirred at room temperature for 4 hours after which time the lithium had completely dissolved. The dark blue solution was then warmed to 50° and a solution of 25.4 g. of 15-oxa-1,4-androstadiene-3,17ethylene ketal and 38.8 g. of diphenyl methane in 100 ml. of tetrahydrofuran was added dropwise over a period of 30 minutes. The temperature was maintained at 50°–52° and the mixture was stirred for an additional hour. The reaction was then cooled to 0° and 45 g. of ammonium chloride was added in small portions (color changed from dark green to light brown). Small pieces of ice were then cautiously added causing the reaction to become colorless, followed by the addition of 100 ml. of ice water. The resulting two layers were separated and the aqueous solution extracted with methylene chloride. The organic layers were combined, dried ($MgSO_4$), and the solvent removed under reduced pressure to give an oily residue. Hexane (800 ml.) was added and the mixture stirred until precipitation took place. The crude precipitate (25 g.) was dissolved in a minimum of methylene chloride and passed through 250 g. of silica gel. Elution with 1% ethyl acetate-benzene and 5% ethyl acetatebenzene gave 15.5 g. of 15-oxaestrone-17-ethylene ketal. Trituration with hexane-ether gave 12.5 g., mp 212°–215°. Crystallization from methylene chloride-ether afforded an analytical sample, mp 214°–216°, $[\alpha]_D^{25}$ +18.99° (c, 0.89%, $CHCl_3$).

Anal. Calcd. for $C_{19}H_{24}O_4$: C, 72.12; H, 7.65. Found: C, 71.98; H, 7.53.

EXAMPLE 14

15-Oxaestrone

A solution of 12 g. of 15-oxaestrone-17-ethylene ketal, 250 ml. of dioxane, and 20 ml. of an 8% aqueous sulfuric acid solution was stirred and refluxed for 4 hours. The solution was cooled, poured into 2 l. of ice water and the precipitate filtered. The product was washed thoroughly with water and air dried. The crude material was then dissolved in a minimum of 1:1 methylene chloride-tetrahydrofuran solution, dried ($MgSO_4$), and heated with charcoal. The mixture was filtered and the solvent removed under reduced pressure. The resulting residue was triturated with ether to give 9.2 g. of 15-oxaestrone. Crystallization from methanol afforded two crops of product: 7.0 g. mp 254°–256°; 1.4 g., mp 252°–254°. Crystallization from methanol of the first crop afforded an analytical sample, mp 255°–256°, $[\alpha]_D^{15}$ +108.45° (c, 0.876%, $CHCl_3$).

Anal. Calcd. for $C_{17}H_{20}O_3$: C, 74.97; H, 7.40. Found: C, 75.28H, 7.84.

EXAMPLE 15

15-Oxaestradiol

A solution of 0.5 g. of 15-oxaestrone in 10 ml. of dry tetrahydrofuran was added dropwise with stirring to a cooled (0°) solution of 1.35 g. of lithium tri-t-butoxyaluminum hydride in 50 ml. of dry tetrahydrofuran. After 15 minutes at 0° chloroform (100 ml.) was added and the mixture washed with cold 1N hydrochloric acid. The solution was then dried ($MgSO_4$) and the solvent removed under reduced pressure. The crude semi-solid was crystallized from acetone-water to give 0.4 g. of 15-oxaestradiol, mp 180°–182°, $[\alpha]_D^{25}$ +74.91° (c, 0.949%, $CH_3OH$).

Anal. Calcd. for $C_{17}H_{22}O_3$: C, 74.42; H, 8.08. Found: C, 74.11; H, 8.19.

EXAMPLE 16

15-Oxa-3-methoxy-19-nor-17α-pregna-1,3,5-(10)-trien-20-yn-17-ol

To a dioxane solution (48 ml.) saturated with acetylene at 0° was added 4.8 g. of lithium acetylide-ethylene diamine followed by the dropwise addition (30 min.) of 0.8 g. of 15-oxaestrone dissolved in 16 ml. of dry dioxane. During the addition and for 40 minutes thereafter acetylene was bubbled through the reaction mixture. The reaction was then stirred at room temperature for 3.5 hours after which time 100 ml. of 20% hydrochloric acid was added slowly with stirring at 0°. The mixture was then extracted with ether, and the ether solution washed with 0.1N hydrochloric acid, water, and then dried ($MgSO_4$). The solvent was then removed under reduced pressure to afford 15-oxa-3-hydroxy-19-nor-17α-pregna-1,3,5(10)-trien-20-yn-17-ol. This was treated directly for 3 days with an ethereal solution of diazomethane. When the reaction was complete (tlc) the solvent and excess diazomethane were blown off by a stream of nitrogen and the resulting product dissolved in a minimum of benzene and passed through 1 g. of silica gel. Elution with benzene afforded 0.75 g. of crude material which when triturated with hexane gave 0.57 g. of 15-oxa-3-methoxy-19-nor-17α-pregna-1,3,5(10)-trien-20-yn-17-ol, mp 112°–124°. Drying at 95°/0.1 mm for 18 hours afforded 0.5 g., mp 140°–142°, $[\alpha]_D^{25}$ 0° (c, 0.8725%, $CHCl_3$).

Anal. Calcd for $C_{20}H_{24}O_3$: C, 76.64; H, 8.04. Found: C, 76.74; H, 7.80.

EXAMPLE 17

3β,17β-Dihydroxy-17α-methyl-15-oxa-5α-androstane

To a solution of 2 g. of 3β-hydroxy-15-oxa-5α-androstan-17-one dissolved in 20 ml. of dry tetrahydrofuran was added dropwise at −70°, 10.8 ml. of a 1.9 molar solution of methyl lithium in ether. The resulting thick gelatinous mass was stirred for 10 minutes and then added to 100 ml. of a 5% aqueous solution of sodium dihydrogen phosphate. The mixture was then extracted with methylene chloride, the solution dried (MgSO$_4$), and the solvent removed under reduced pressure. The residue was then crystallized from acetone to give 1.5 g. of 3β,17β-dihydroxy-17α-methyl-15-oxa-5α-androstane, mp 227°–229°, $[\alpha]_D^{25}$ −13.58° (c, 0.5303%, CHCl$_3$).

Anal. Calcd. for C$_{19}$H$_{32}$O$_3$: C, 73.98; H, 10.46. Found: C, 73.67; H, 10.76.

EXAMPLE 18

17β-Hydroxy-17α-methyl-15-oxa-5α-androstan-3-one

To a suspension of 1.8 g. of crude 3β,17β-dihydroxy-17α-methyl-15-oxa-5α-androstane in 20 ml. of acetone was added with stirring at 0° 2 ml. of Jones reagent. Dissolution soon occurred and after 10 minutes the oxidation was found to be complete (tlc). The solution was then poured into 100 ml. of ice water, and the reaction mixture extracted with methylene chloride after saturation of the aqueous solution with sodium chloride. The organic layer was dried (MgSO$_4$) and the solvent removed under reduced pressure to give 1.5 g. of 17β-hydroxy-17α-methyl-15-oxa-5α-androstan-3-one. Crystallization from methylene chloride-ether afforded an analytical sample, mp 196°–198°, $[\alpha]_D^{25}$ +6.43° (c, 0.9646%, CHCl$_3$).

Anal. Calcd. for C$_{19}$H$_{30}$O$_3$: C, 74.47; H, 9.87. Found: C, 74.73; H, 10.08.

EXAMPLE 19

15-Oxa-17β-hydroxy-17α-methyl-5α-androstane[3,2-c]pyrazole

A solution of 2.5 g. of 17β-hydroxy-17α-methyl-15-oxa-5α-androstan-3-one, 0.84 g. of sodium methoxide, 4.6 ml. of ethyl formate and 25 ml. of pyridine was stirred under nitrogen for 18 hours. The mixture was then poured into 300 ml. of ice water containing 46 ml. of glacial acetic acid. The resulting precipitate was filtered, washed with water and dissolved in a small amount of ether. The cloudy solution was dried (MgSO$_4$) and the solvent removed under reduced pressure to give 2 g. of white crystalline (2-formyl-17β-hydroxy-17α-methyl-15-oxa-5α-androstan-3-one), mp 262°–269°; $\lambda_{max}^{C_2H_5OH}$ 285 (ε7,430).

A solution of 2 g. of the formylated material, 50 ml. of absolute ethanol and 0.48 ml. of hydrazine hydrate (85%) was refluxed for one hour. The ethanol was removed under reduced pressure and the residue triturated with ether to give 1.8 g. of 15-oxa-17β-hydroxy-17α-methyl-5α-androstan[3,2-c]pyrazole. Crystallization from chloroform afforded an analytical sample, mp 175° d, $[\alpha]_D^{25}$ +31.45° (c, 0.9826%, CH$_3$OH).

Anal. Calcd. for C$_{20}$H$_{30}$N$_2$O$_2$: C, 72.69; H, 9.15; N, 8.50. Found: C, 72.86; H, 8.77; N, 8.31.

EXAMPLE 20

15-Oxaestrone cyclopentyl ether

A solution of 0.29 g. of 15-oxaestrone, 3 ml. of absolute ethanol, 1 ml. of cyclopentyl bromide and 1.5 ml. of a lithium methoxide-methanol solution (10.23%, sp gr. 0.853) was refluxed for 18 hours. The solution was then poured into 50 ml. of water and the mixture extracted with methylene chloride. The methylene chloride solution was then dried (MgSO$_4$) and most of the solvent removed under reduced pressure. The residue was then passed through a 3 g. of neutral alumina (grade 1) and the product crystallized from methylene chloride-ether to give 0.2 g. of 15-oxaestrone cyclopentyl ether, mp 198°–201°, $[\alpha]_D^{25}$ +117.85° (c, 1.125%, CHCl$_3$).

Anal. Calcd. for C$_{22}$H$_{28}$O$_3$: C, 77.61; H, 8.29. Found: C, 77.75; H, 8.58.

EXAMPLE 21

Estrone 3-methyl ether was converted to 3-methoxy-16,17-seco-16-norestra-1,3,5(10)trien-15-(2'-indoxyliden)-17-oic acid, mp 255°–257° according to the procedure of example 1. The material was converted to the methyl ester, i.e. 3-methoxy-16,17-seco-16-norestra-1,3,5(10)-trien-15-(2'-indoxyliden)-17-oic acid 17-methyl ester, mp 259°–260° (dec.), according to the procedure of example 2.

EXAMPLE 22

3-Methoxy-16,17-seco-16-norestra-1,3,5(10)-trien-15-(2'-indoxyliden)-17-oic acid 17-methyl ester was converted to 15-oxaestrone 3-methyl ether according to the procedures in examples 4 through 8 via the following intermediates:

3-methoxy-15,17-seco-D-norestra-1,3,5(10)-trien-15,17-dioic acid 17-methyl ester,
3-methoxy-14β-acetoxy-14,17-seco-D-bisnorestra-1,3,5(10)-trien-17-oic acid 17-methyl ester,
3-methoxy-14β-hydroxy-14,17-seco-D-bisnorestra-1,3,5(10)-trien-17-oic acid,
3-methoxy-14β-acetoxy-14,17-seco-D-bisnorestra-1,3,5(10)-trien-17-oic acid,
3-methoxy-14β-acetoxy-16-diazo-17-oxo-14,16-seco-D-norestra-1,3,5(10)-triene, and
3-methoxy-14β-hydroxy-16-diazo-17-oxo-14,16-seco-D-norestra-1,3,5(10)-triene.

EXAMPLE 23

Estrone was converted to 15-oxaestrone according to the procedures in examples 1 through 8 via the following intermediates:

3-hydroxy-16,17-seco-16-norestra-1,3,5(10)-trien-15-(2'-indoxyliden)-17-oic acid,
3-hydroxy-16,17-seco-16-norestra-1,3,5(10)-trien-15-(2'-indoxyliden)-17-oic acid 17-methyl ester,
3-acetoxy-16,17-seco-16-norestra-1,3,5(10)-trien-15-(2'-indoxyliden)-17-oic acid 17-methyl ester,
3-acetoxy-15,17-seco-D-norestra-1,3,5(10)-trien-15,17-dioic acid 17-methyl ester,
3,14β-diacetoxy-14,17-seco-D-bisnorestra-1,3,5(10)-trien-17-oic acid 17-methyl ester,
3-hydroxy-14β-acetoxy-14,17-seco-D-bisnorestra-1,3,5(10)-trien-17-oic acid 17-methyl ester,
3,14β-dihydroxy-14,17-seco-D-bisnorestra-1,3,5(10)-trien-17-oic acid, 3,14β-diacetoxy-14,17-seco-D-bisnorestra-1,3,5(10)-trien-17-oic acid,
3,14β-diacetoxy-16-diazo-17-oxo-14,16-seco-D-norestra-1,3,5(10)-triene, and
3,14β-dihydroxy-16-diazo-17-oxo-14,16-seco-D-norestra-1,3,5 (10)-triene.

EXAMPLE 24

15-Oxaestrone 3-methyl ether was converted to 15-oxa-19-nortestosterone, according to well known procedures for the conversion of estrone 3-methyl ether to 19-nortestosterone, i.e. lithium-ammonia reduction to 3-methoxy-15-oxa-estra-2,5(10)dien-17β-ol followed by strong acid acid hydrolysis. 15-oxa-19-nortestosterone was converted to 15-oxa-19-norandrost-4-en-3,17-dione by oxidation with chromium trioxide.

EXAMPLE 25

15-Oxaestrone 3-methyl ether was converted to 15-oxa-19-norprogesterone, according to the procedure in U.S. Pat. No. 3,385,849, via the following intermediates:

3-methoxy-15-oxa-19-norpregna-1,3,5(10),17(20)-tetraene,
3-methoxy-15-oxa-19-norpregna-1,3,5(10)-trien-20-ol,
3-methoxy-15-oxa-19-norpregna-2,5(10)-dien-20-ol, and
15-oxa-19-norpregn-4-en-3-on-20-ol

EXAMPLE 26

15-Oxa-19-norandrost-4-en-3,17-dione was converted to 17α-ethynyl-15-oxa-19-norandrost-4-en-3-on-17β-ol according to well known procedures for ethynylation of 19-norandrost-4-en-3,17-dione, in U.S. Pat. No. 2,962,509.

I claim:
1. A compound of the formula

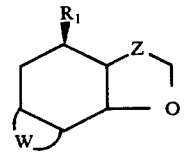

wherein $R_1$ is lower alkyl of from 1 to 5 carbon atoms; W is

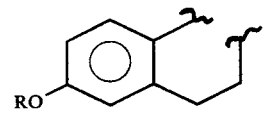

wherein R is hydrogen, lower alkyl, cycloalkyl, lower alkanoyl or aroyl and Z is ketal protected carbonyl selected from the group consisting of ethylenedioxymethylene, 1,3-propylenedioxymethylene and 2,3-butylenedioxymethylene.

2. The compound of claim 1 wherein $R_1$ is methyl.

3. The compound of claim 2 which is 15-oxaestrone 17-ethylene ketal.

* * * * *